United States Patent
Drewry et al.

(10) Patent No.: US 7,625,380 B2
(45) Date of Patent: Dec. 1, 2009

(54) DUAL DISTRACTOR INSERTER

(75) Inventors: Troy D. Drewry, Memphis, TN (US); Bret M. Berry, Jacksonville, FL (US)

(73) Assignee: Warsaw Orthopedic, Inc.

( * ) Notice: Subject to any disclaimer, the term of this patent is extended or adjusted under 35 U.S.C. 154(b) by 783 days.

(21) Appl. No.: 10/896,290

(22) Filed: Jul. 21, 2004

(65) Prior Publication Data
US 2006/0030856 A1 Feb. 9, 2006

(51) Int. Cl.
*A61B 17/58* (2006.01)
*A61B 17/60* (2006.01)
*A61F 2/00* (2006.01)

(52) U.S. Cl. .......................... 606/99; 606/90; 606/105; 606/914

(58) Field of Classification Search .................. 606/86, 606/90, 99, 105, 86 A, 914
See application file for complete search history.

(56) References Cited

U.S. PATENT DOCUMENTS

| | | | |
|---|---|---|---|
| 3,678,934 A | 7/1972 | Warfield, et al. | |
| 3,841,335 A | 10/1974 | Tarsitano | |
| 4,589,414 A | 5/1986 | Yoshida et al. | |
| 4,985,031 A | 1/1991 | Buss et al. | |
| 5,092,869 A | 3/1992 | Waldron | |
| 5,201,749 A | 4/1993 | Sachse et al. | |
| 5,330,479 A | 7/1994 | Whitmore | |
| 5,387,215 A | 2/1995 | Fisher | |
| 5,445,639 A | 8/1995 | Kuslich et al. | |
| 5,571,109 A | 11/1996 | Bertagnoli | |
| 5,697,977 A | 12/1997 | Pisharodi | |
| 5,782,830 A * | 7/1998 | Farris | 606/61 |
| 5,797,909 A | 8/1998 | Michelson | |
| 5,846,244 A | 12/1998 | Cripe | |
| 5,928,239 A | 7/1999 | Mirza | |
| 5,976,137 A | 11/1999 | Mayer | |
| 6,048,345 A | 4/2000 | Berke et al. | |
| 6,083,228 A | 7/2000 | Michelson | |
| 6,096,038 A | 8/2000 | Michelson | |
| 6,159,215 A * | 12/2000 | Urbahns et al. | 606/86 |
| 6,224,604 B1 | 5/2001 | Suddaby | |
| 6,258,125 B1 | 7/2001 | Paul et al. | |
| 6,261,296 B1 | 7/2001 | Aebi et al. | |
| 6,319,257 B1 * | 11/2001 | Carignan et al. | 606/99 |
| 6,368,325 B1 | 4/2002 | McKinley et al. | |
| 6,652,533 B2 * | 11/2003 | O'Neil | 606/100 |
| 2001/0034526 A1 | 10/2001 | Kuslich et al. | |
| 2002/0045904 A1 * | 4/2002 | Fuss et al. | 606/99 |
| 2005/0027300 A1 * | 2/2005 | Hawkins et al. | 606/86 |
| 2005/0143747 A1 * | 6/2005 | Zubok et al. | 606/90 |
| 2005/0203538 A1 * | 9/2005 | Lo et al. | 606/99 |

FOREIGN PATENT DOCUMENTS

| | | |
|---|---|---|
| EP | 1093760 A2 | 4/2001 |
| EP | 1129668 A1 | 9/2001 |

(Continued)

OTHER PUBLICATIONS

Patent Cooperation Treaty—European Patent Office, "Notification of Transmittal of the International Search Report and the Written Opinion of the International Searching Authority, or the Declaration," International Application No. PCT/US2005/025778, Nov. 7, 2005, 13 pages.

*Primary Examiner*—Thomas C Barrett
*Assistant Examiner*—Andrew Yang

(57) ABSTRACT

In one embodiment, there is disclosed a surgical instrument for inserting an implant, the surgical instrument including an inserter assembly and a distractor assembly.

9 Claims, 10 Drawing Sheets

FOREIGN PATENT DOCUMENTS

| | | |
|---|---|---|
| EP | 1260187 A1 | 11/2002 |
| EP | 1283026 A2 | 2/2003 |
| EP | 1 323 396 | 7/2003 |
| EP | 1342457 A2 | 9/2003 |
| EP | 1346695 A1 | 9/2003 |
| WO | WO 03/077808 | 9/2003 |

* cited by examiner

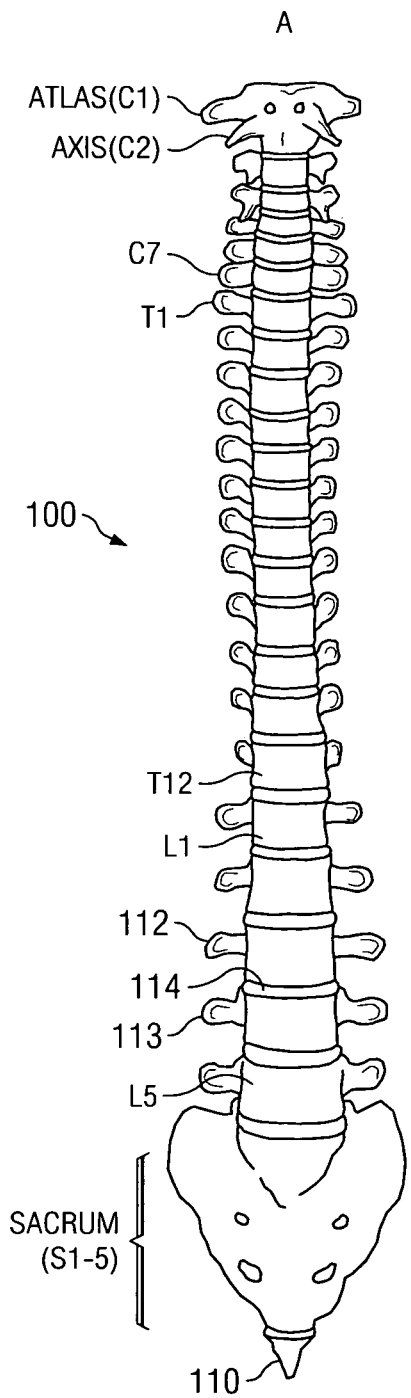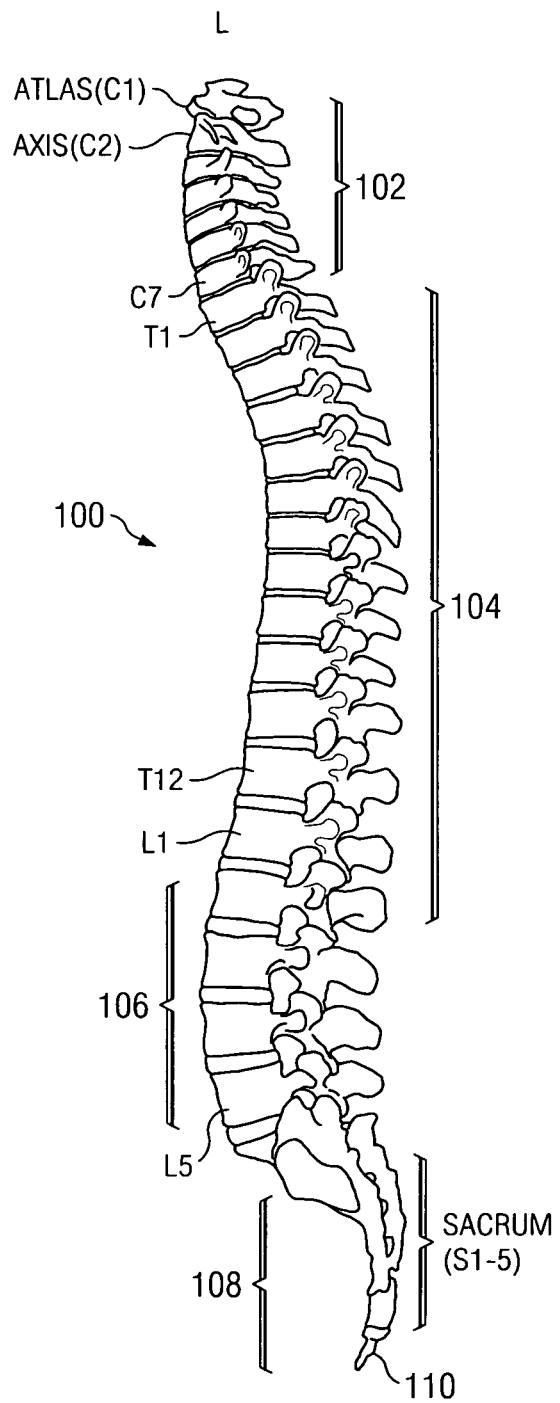
*Fig. 1A*
(PRIOR ART)
*Fig. 1B*
(PRIOR ART)

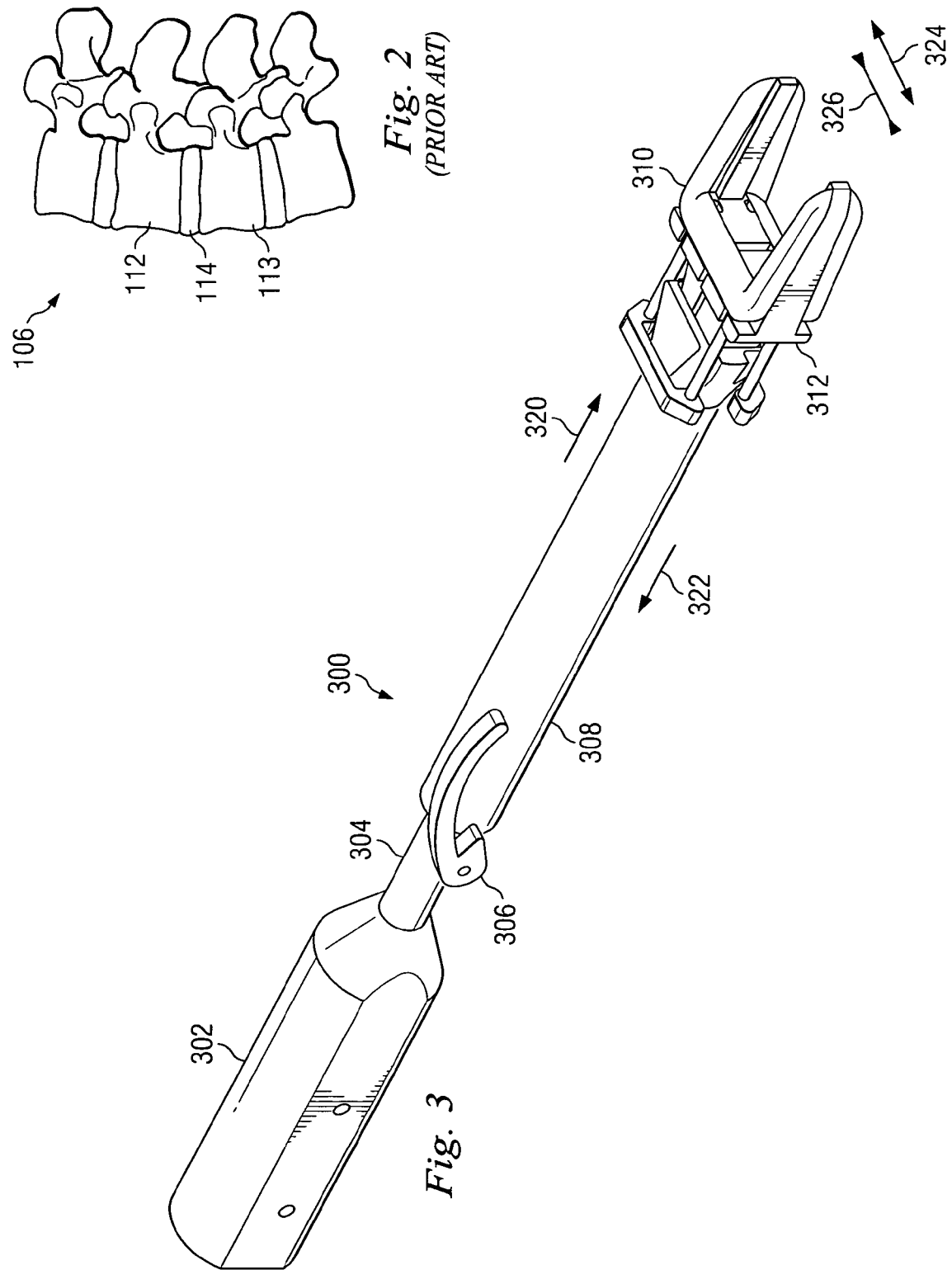

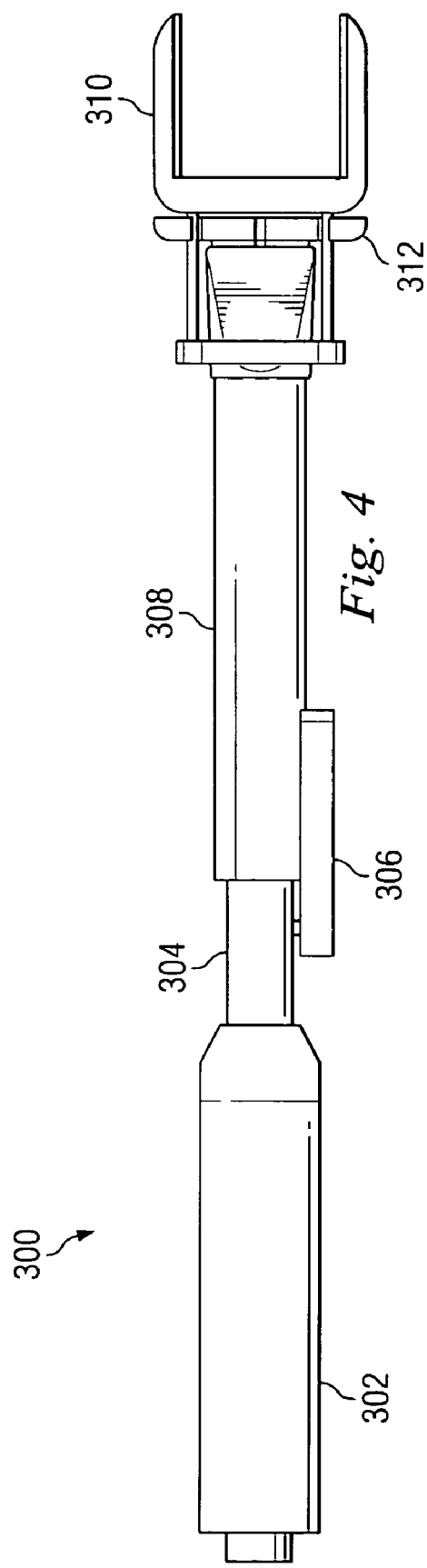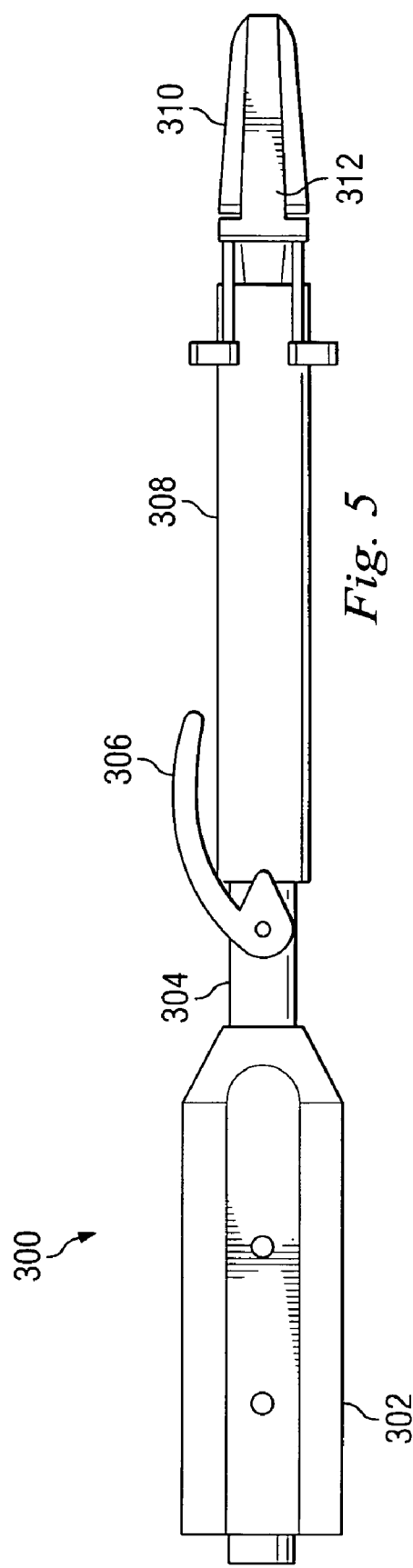

DUAL DISTRACTOR INSERTER

FIELD

The present disclosure generally relates to surgical instruments for use in the insertion of implants.

BACKGROUND

Intervertebral discs, located between the end plates of adjacent vertebrae, stabilize the spine, distribute forces between the vertebrae and cushion the vertebral bodies. An intervertebral disc might deteriorate due to trauma, aging, or disease, resulting in pain or discomfort to a patient. One common procedure for relief of patient discomfort is a discectomy, or surgical removal of all or part of the intervertebral disc. Often, this is followed by implantation of a device or spinal implant between the adjacent vertebrae in order to maintain or restore disc space height. Through stabilization of the vertebrae, the risk of reoccurrence of the same disabling back pain due to persistent inflammation and/or instability is reduced.

During implantation of the spinal implant, the end plates of adjacent vertebrae are sometimes milled to ensure firm implantation of the spinal implant by promoting bone ingrowth. One suitable tool for preparing the endplates is disclosed in PCT serial number PCT/IB0300910, filed on Mar. 13, 2003, in the name of SDGI Holdings, Inc. PCT/IB0300910 is herein incorporated by reference in its entirety.

Referring to FIG. 1, there is illustrated spine 100. At A is an anterior view of spine 100, and at L is a left lateral view of spine 100. Spine 100 includes cervical curvature 102, C1-C7; thoracic curvature 104, T1-T12; lumbar curvature 106, L1-L5; sacral curvature 108, S1-S5; and coccyx 110. Vertebrae L3 112 and vertebrae L4 113 are shown. Intervertebral disc 114 is shown between L3 112 and L4 113.

Referring to FIG. 2, is there is illustrated a close-up view of lumbar curvature 106. As discussed above regarding FIG. 1, L3 112 intervertebral disc 114, and L4 113 are shown.

If a patient has a problem with intervertebral disc 114, all or a portion of disc 114 can be removed and replaced with an insert (not shown).

A need exists in the pertinent art for a surgical tool which permits improved implantation of an insert.

SUMMARY

In one embodiment, there is disclosed a surgical instrument for inserting an implant, the surgical instrument including an inserter assembly and a distractor assembly.

Additional advantages and features of the present disclosure will become apparent from the following description and appended claims, taken in conjunction with the accompanying drawings.

Further areas of applicability of the present disclosure will become apparent from the detailed description provided hereinafter. It should be understood that the detailed description and specific examples, while indicating several alternative embodiments, are intended for purposes of illustration only and are not intended to limit the scope of the claims.

BRIEF DESCRIPTION OF THE DRAWINGS

The present disclosure will become more fully understood from the detailed description and the accompanying drawings, wherein:

FIG. 1 is a prior art illustration of a spine.

FIG. 2 is a prior art illustration of the lumbar curvature of a spine.

FIG. 3 is a perspective view of an embodiment of a surgical instrument.

FIG. 4 is a top view of an embodiment of a surgical instrument.

FIG. 5 is a side the top view of an embodiment of a surgical instrument.

DETAILED DESCRIPTION

Figure 6:
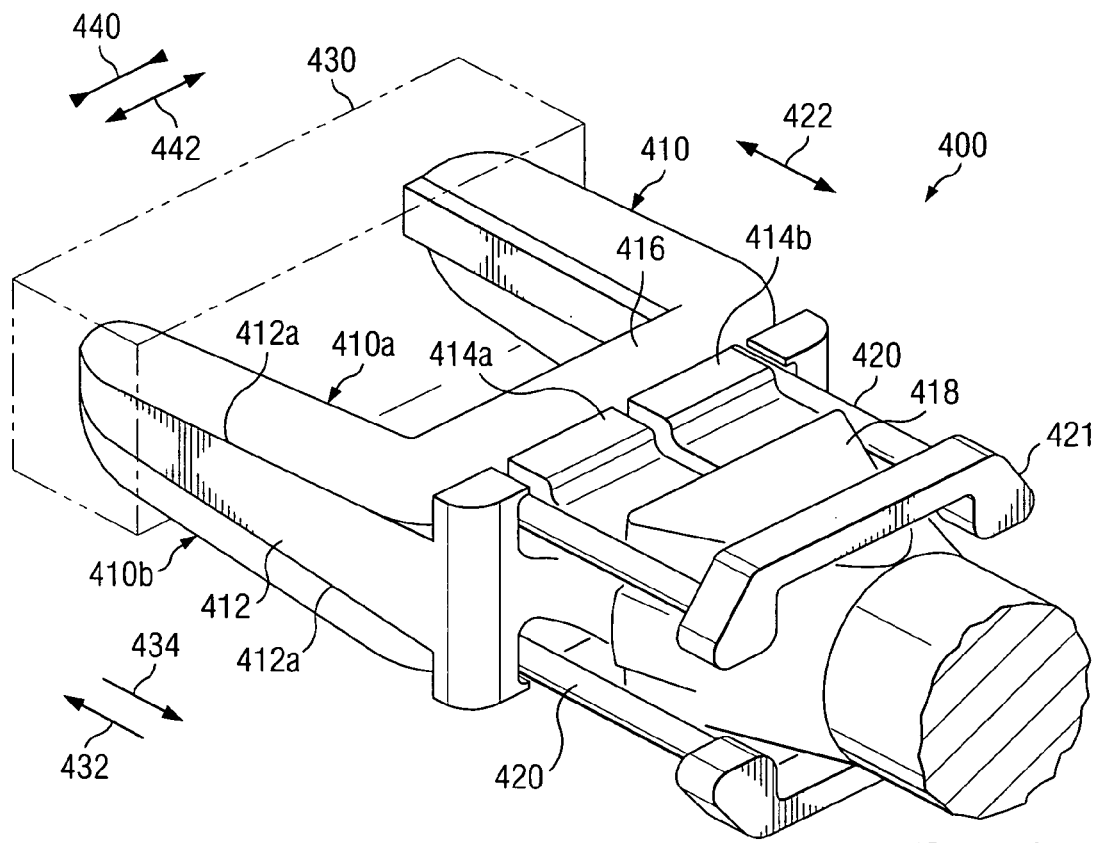
FIG. 6 is a perspective view of an embodiment of the distal end of a surgical instrument.

The following description of several alternative embodiments is merely exemplary in nature and is in no way intended to limit the scope of the claims, or their application, or uses.

Referring now to FIGS. 3-5, in one embodiment, there is shown various views of a surgical instrument. Surgical instrument 300 includes handle 302, shaft 304, cam 306, compression sleeve 308, distractor tangs 310, and inserter tangs 312.

In operation, distractor tangs 310 ride on inserter tangs 312. As inserter tangs 312 are displaced proximally, as shown by arrow 320, relative to distractor tangs 310, distractor tangs 310 are able to close. Alternatively, as inserter tangs 312 are displaced distally, as shown by arrow 322, relative to distractor tangs 310, distractor tangs 310 are forced by inserter tangs 312.

As compression sleeve 308 is moved proximally, as shown by arrow 320, relative to inserter tangs 312, inserter tangs 312 open laterally, as shown by arrows 324. Alternatively, cam 306 may be used to forced compression sleeve 308 distally, as shown by arrow 322, relative to inserter tangs 312, which forces inserter tangs medially, as shown by arrows 326.

In one embodiment, handle 302 is fixedly connected to shaft 304; cam 306 is rotationally connected to shaft 304; cam 306 may be used to forced compression sleeve 308 distally, as shown by arrow 322; compression sleeve 308 may be used to force inserter tangs 312 medially, as shown by arrow 326; inserter tangs 312 may be moved distally, as shown by arrow 322, to force open distractor tangs 310; and/or inserter tangs 312 may be moved proximally, as shown by arrow 320, to allow distractor tangs 310 to close.

Referring to FIG. 6, in another embodiment, distal portion 400 of a surgical tool is shown. Distal portion 400 includes distractor tangs 410, inserter tangs 412, distal portion of compression tube 418, proximal portion of distractor tangs 416, proximal portions of inserter tangs 414a and 414b, arms of distractor tangs 420, and arm connector 421.

In operation, inserter tangs 412 may be used to hold an insert or an implant (not shown). The insert may be placed between inserter tangs 412, then distal portion of tube 418 may be moved distally, as shown by arrow 432, relative to inserter tangs 412. Distal portion of tube 418 by this distal movement, forces together proximal portions of inserter tangs 414a and 414b, which also forces inserter tangs 412 medially, as shown by arrows 440. Distal portion of tube 418 may be used to hold the insert between inserter tangs 412, until distal portion of tube 418 is moved proximally relative to inserter tangs 412, as shown by arrow 434.

Once the insert is held between inserter tangs 412, distal portion of inserter tool 400 may be moved distally, as shown by arrow 432, until distal portion 400 encounters tissue 430. Tissue 430 impedes distal movement of distractor tangs 410. Tissue 430 pushes distractor tangs 410 proximally relative to the rest of the tool, until proximal portion of distractor tangs 416 encounters proximal portions of inserter tangs 414a and 414b. Proximal portions of inserter tangs 414a and 414b then force distractor tangs 410 distally with the rest of the tool. Inserter tangs 412 have inclined surfaces 412a, which force open distractor tangs 412, as inserter tangs 412 and surfaces 412a move distally relative to distractor tangs 410.

Distractor tangs 410 are then forced fully open by inserter tangs 412 and surfaces 412a, when proximal portion 416 engages proximal portions 414a and 414b. Distractor tangs 410 create an opening in tissue 430 as distal end 400 moves into tissue 430. Distal end of tool 400 is moved distally into tissue 430, until the insert is located in the preferred position.

Once the insert is located, distal portion of tube 418 is moved proximally relative to inserter tangs 412, as shown by arrow 434, inserter tangs 412 are released laterally, as shown by arrows 442. As the inserter tangs 412 are released, the insert is released.

To remove distal end of tool 400 from tissue 430, inserter tangs 412 are first moved proximally relative to distractor tangs 410, as shown by arrow 434. As inserter tangs 412, having inclined surfaces 412a, are moved proximally, distractor tangs 412 are able to close, as inclined surfaces 412a are no longer supporting or holding open distractor tangs 410. With the continued proximal movement of inserter tangs 412, proximal portions 414a and 414b engage arm connector 421. Once proximal portions 414a and 414b have engaged arm connector 421, continued proximal movement of inserter tangs 412 also causes proximal movement of distractor tangs 410, until all of distal end of tool 400 has been removed from tissue 430.

Figure 7:
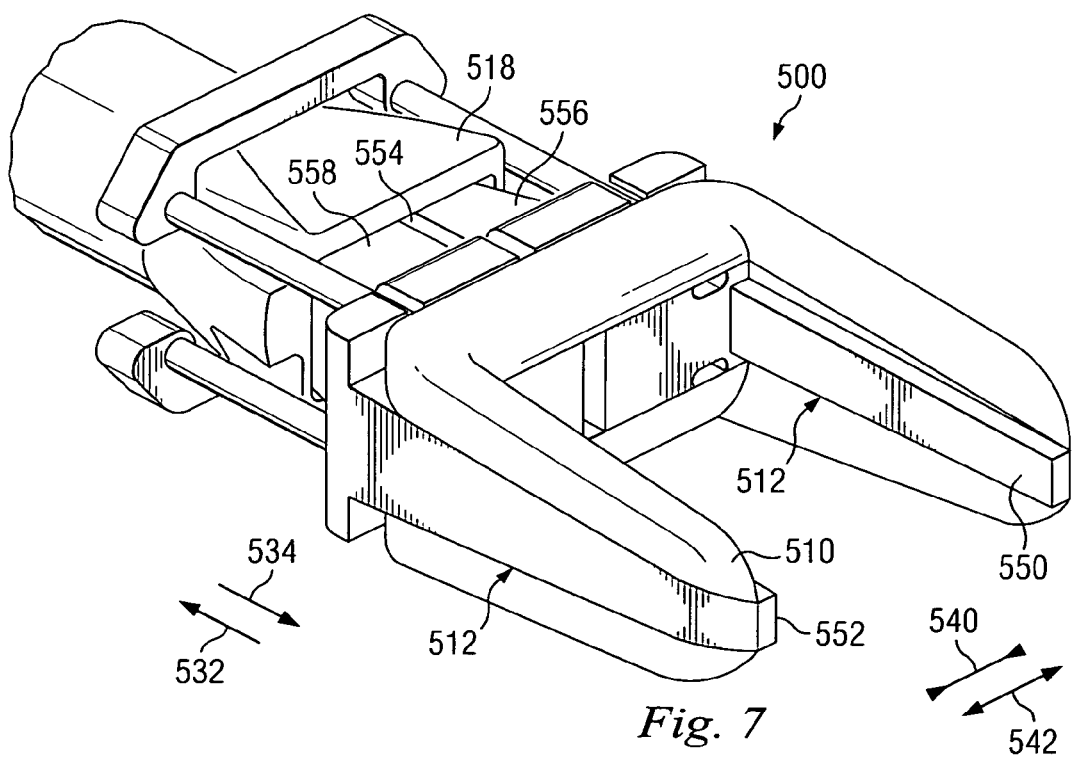
FIG. 7 is a perspective view of an embodiment of the distal end of a surgical instrument.

Referring to FIG. 7, in another embodiment, there is illustrated distal end of tool 500. Distal end of tool 500 includes distractor tangs 510, inserter tangs 512, and distal end of compression tube 518. Inserter tangs 512 include left inserter tang 550 coupled to left inserter bracket 556, right inserter tang 552 coupled to right inserter bracket 558, with space 554 between left inserter tang 550 and right inserter tang 552.

In operation, inserter tangs 512 may be used to grip an implant or an insert (not shown). The implant may be placed between left inserter tang 550 and right inserter tang 552. Distal end of tube 518 may then be moved distally, as shown by arrow 532, relative to inserter tangs 512. This distal movement of distal end of tube 518, forces left inserter bracket 556 and right inserter bracket 558 medially, as shown by arrows 540. The medial movement of left inserter bracket 556 causes medial movement of left inserter tang 550, and the medial movement of right inserter bracket 558 causes medial movement of right inserter tang 552. The medial movement of inserter tangs 512 closes space 554, and allows the insert to be held by inserter tangs 512.

To release the insert, distal end of tube 518 is moved proximally relative to inserter tangs 512, as shown by arrow 534. This proximal movement allows left inserter bracket 556 and right inserter bracket 558 to move laterally, as shown by arrows 542. The lateral movement of left inserter bracket 556 causes lateral movement of left inserter tang 550, and the lateral movement of right inserter bracket 558 causes lateral movement of right inserter tang 552. The lateral movement of inserter tangs 512 opens space 554, and allows the insert to be released.

In one embodiment, inserter tangs 512 are biased laterally, as shown by arrows 542, for example by a spring, or left inserter bracket 556 and right inserter bracket 558 being bent laterally. This lateral biasing can be overcome by moving distal end of tube 518 distally relative to inserter tangs 512. The lateral biasing can be recovered by moving distal end of tube 518 proximally relative to inserter tangs 512.

Figure 8:
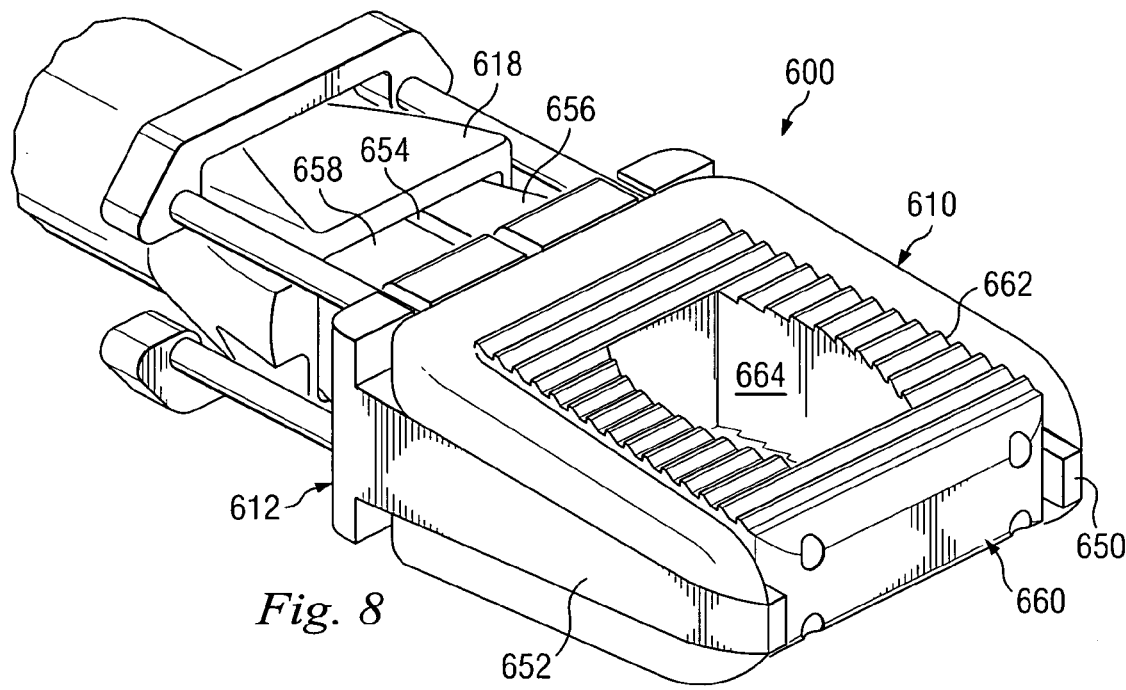
FIG. 8 is a perspective view of an embodiment of the distal end of a surgical instrument with an insert.

Referring now to FIG. 8, in another embodiment, there is illustrated distal end of tool 600. Distal end of tool 600 includes distractor tangs 610, inserter tangs 612, and distal end of compression tube 618. Inserter tangs 612 include left inserter tang 650 coupled to left inserter bracket 656, right inserter tang 652 coupled to right inserter bracket 658, with space 654 between left inserter tang 650 and right inserter tang 652.

In operation, inserter tangs 612 may be used to grip implant 660. Implant 660 includes rough surface 662, and has hole 664 defined therethrough. Implant 660 is shown held between left inserter tang 650 and right inserter tang 652, due to a distal movement of tube 618 forcing left inserter bracket 656 and right inserter bracket 658 medially, and closing space 654.

To release implant 660, distal end of tube 618 is moved proximally relative to inserter tangs 612. This proximal movement allows left inserter bracket 656 and right inserter bracket 658 to move laterally. The lateral movement of left inserter bracket 656 causes lateral movement of left inserter tang 650, and the lateral movement of right inserter bracket 658 causes lateral movement of right inserter tang 652. The lateral movement of inserter tangs 612 opens space 654, and allows implant 660 to be released.

Figure 9:
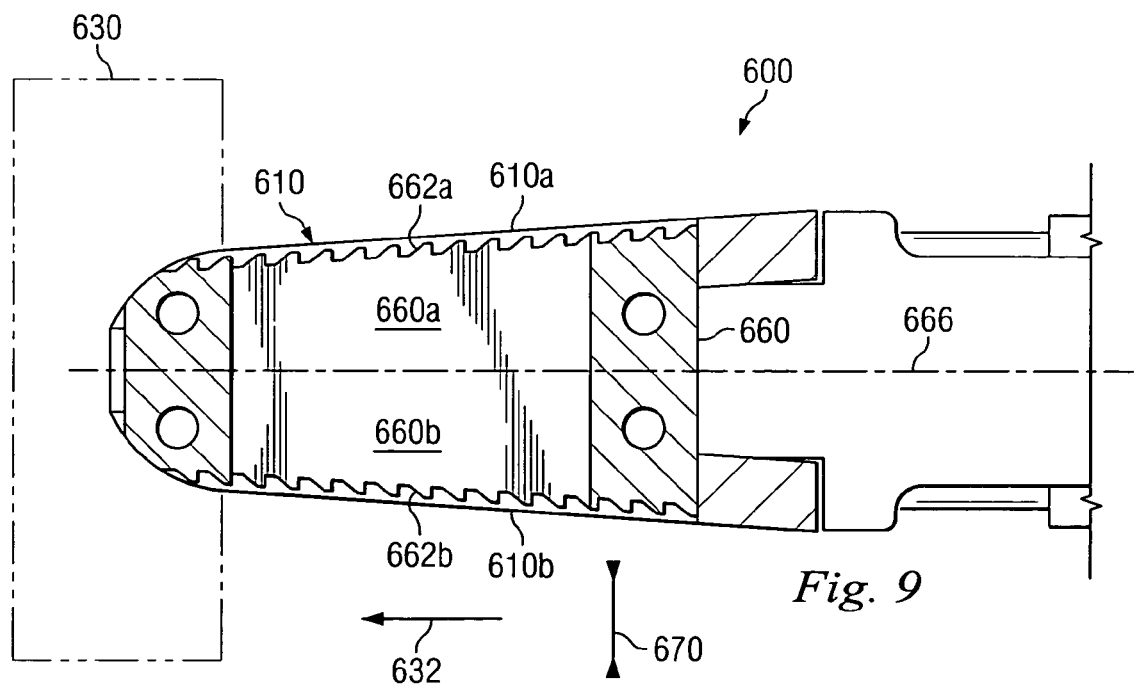
FIG. 9 is a cross-sectional side view of the embodiment shown in FIG. 8.

Referring now to FIG. 9, in another embodiment, there is illustrated a side cross-sectional view of distal end of tool 600 from FIG. 8. Distal end of tool 600 includes distractor tangs 610 and implant 660. Implant 660 includes rough surfaces 662a and 662b. Implant 660 is shown held by distal end of tool 600. Implant 660 includes centerline 666, defining an interior of implant 660. On first side of implant 660a, exterior to centerline 666 is defined rough surface 662a. Exterior to rough surface 662a is surface 610a of distractor tang 610. On second side of implant 660b, exterior to centerline 666 is defined rough surface 662b. Exterior to rough surface 662b is surface 610b of distractor tang 610.

In operation, as distal end of tool 600 is moved distally, as shown by arrow 632, and is fed through tissue 630, tissue 630 is held open by distractor surfaces 610a and 610b. In one embodiment, tissue 630 is not held open by rough surfaces 662a and 662b. In another embodiment, tissue 630 does not touch rough surfaces 662a and 662b, until distractor tangs 610 are closed medially, as shown by arrows 670 and/or until implant 660 is released by distal end of tool 600.

In another embodiment, insert 660 has a thickness less than the opening created between surface 610a and surface 610b, so that rough surfaces 662a and 662b do not engage tissue 630 during insertion. The distraction tangs 610 are positioned to distract the disc space slightly greater than the height of the implant 660. During insertion, this difference in the greater height of the distraction tangs 610 and the lesser height of the implant 660 spares the implant from the potentially damaging forces experienced during the impaction into the disc space. In one embodiment, the distraction tangs 610 are reduced in height in a direction parallel to the force applied by the adjacent vertebrae. The axial force of the spine or load applied by the adjacent vertebrae may then be transferred as a compressive force onto implant 660. In at least one of the disclosed embodiments, the distraction assembly can be operated to provide a gradual transfer of compressive force from the tangs to the implant. In such embodiments, after the distraction tangs have been reduced in height and at least some of the compressive force transferred to the implant 660, the distraction tangs 610 may be more easily withdrawn from the disc space. Further, the addition of compressive force on the implant 660 in a direction substantially parallel to the axis of the spine and perpendicular to the axis of insertion inhibits the movement of the implant as the inserter is withdrawn from the disc space. In one embodiment, a series of removable distraction tangs 610 are provided in various heights to accommodate more than one anticipated implant or distraction height. Therefore, the instrument may be customized by the user to match various implant size and patient anatomy.

Figure 10:
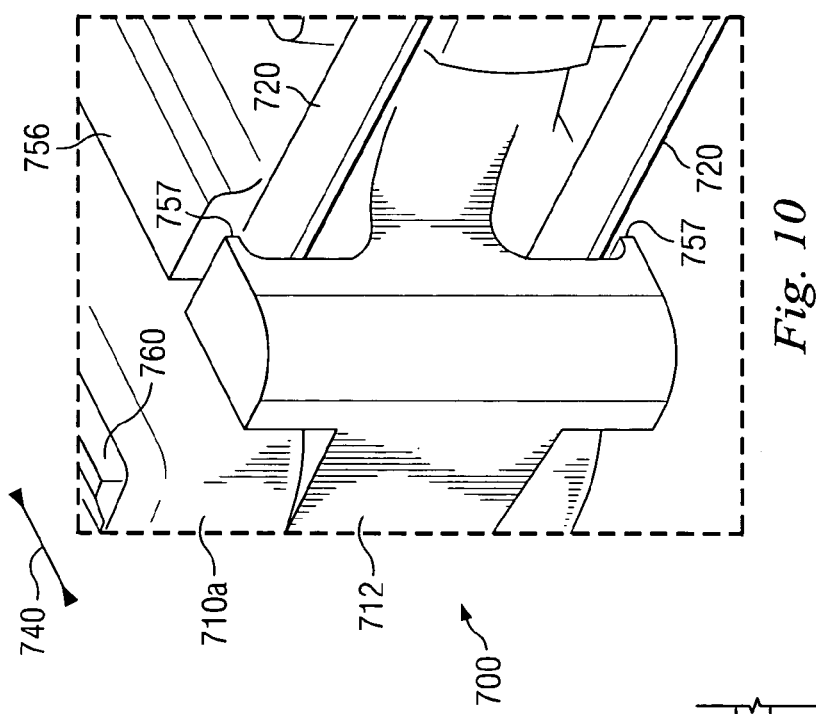
FIG. 10 is a partial perspective view of an embodiment of the distal end of a surgical instrument with an insert.

Referring now to FIG. 10, in another embodiment, there is illustrated a partial view of distal end of tool 700. Distal end of tool 700 includes top distractor tang 710a, inserter tang 712, and distal end of compression tube 718. Inserter tang 712 is coupled to left inserter bracket 756. Left inserter bracket includes lock tabs 757. Top distractor tang 710a and bottom distractor tang (not shown) are attached to arms 720. Arms 720 are fed through lock tabs 757.

In operation, inserter tang 712 may be used to grip implant 760. Arms 720 are initially free to move, but when left bracket 756 moves medially, as shown by arrow 740, arms 720 are constrained by lock tabs 757. As shown, movement of top distractor tang 710a is constrained by insert 760 and inserter bracket 756.

Figure 11:
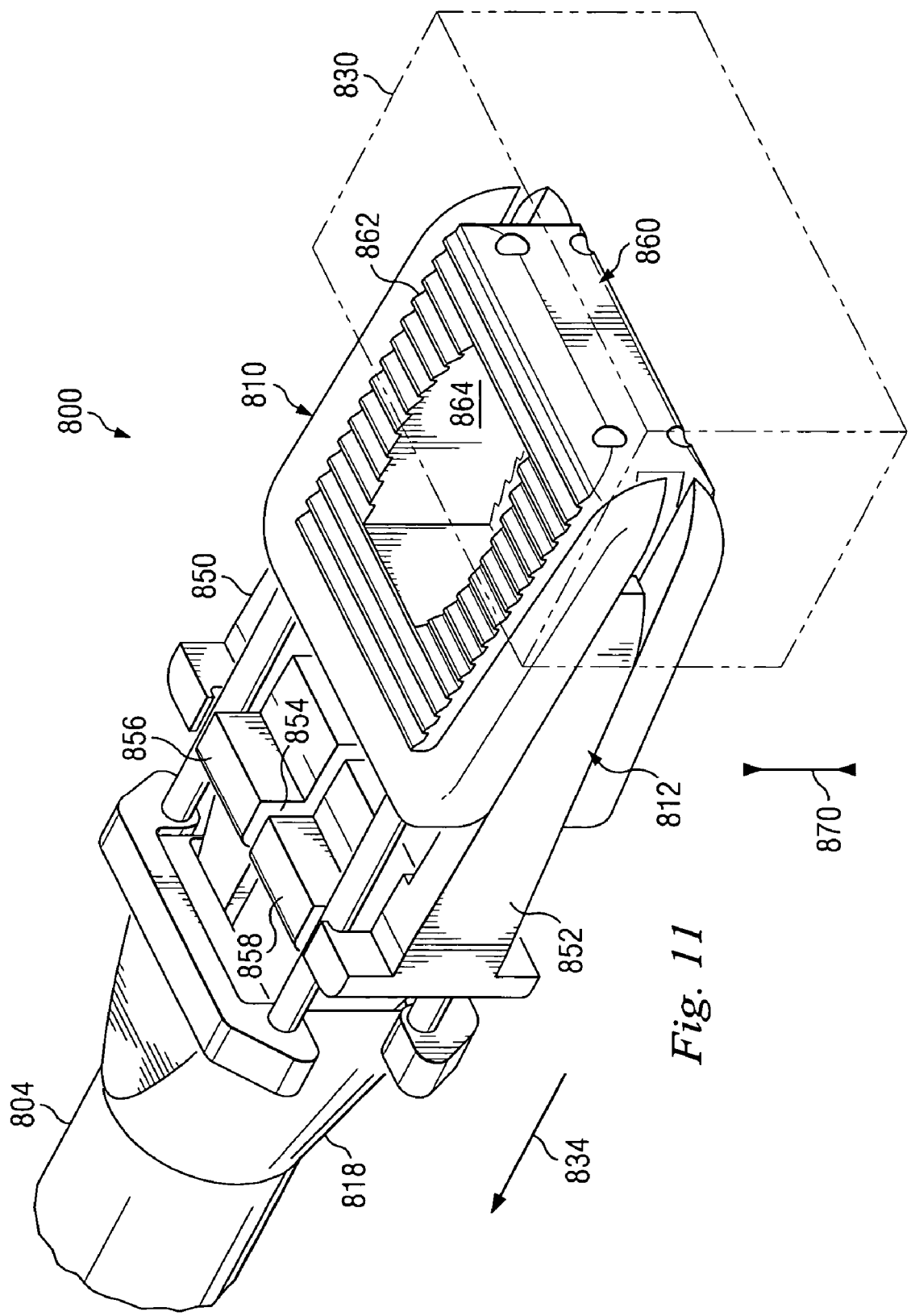
FIG. 11 is a perspective view of an embodiment of the distal end of a surgical instrument with an insert.

Referring now to FIG. 11, in another embodiment, there is illustrated distal end of tool 800. Distal end of tool 800 includes distractor tangs 810, inserter tangs 812, and distal end of compression tube 818. Inserter tangs 812 include left inserter tang 850 coupled to left inserter bracket 856, right inserter tang 852 coupled to right inserter bracket 858, with space 854 between left inserter bracket 856 and right inserter bracket 858.

In operation, inserter tangs 812 are being used to grip implant 860. Implant 860 includes rough surface 862, and has hole 864 defined therethrough. Implant 860 is shown held between left inserter tang 850 and right inserter tang 852, since tube 818 is forcing left inserter bracket 856 and right inserter bracket 858 medially, and closing space 854. Distractor tangs 810 and insert 860 have engaged tissue 830. As distal and 800 is pulled proximally by shaft 804, as shown by arrow 834, inserter tangs 812 move proximally relative to distractor tangs 810 and implant 860. This proximal movement of tool 800 and inserter tangs 812 allows tissue 830 to force distractor tangs 810 medially, as shown by arrows 870. As inserter tangs 812 continue to move proximally, distractor tangs 810 continue to close medially, and expose insert 860 to tissue 830.

Figure 12:
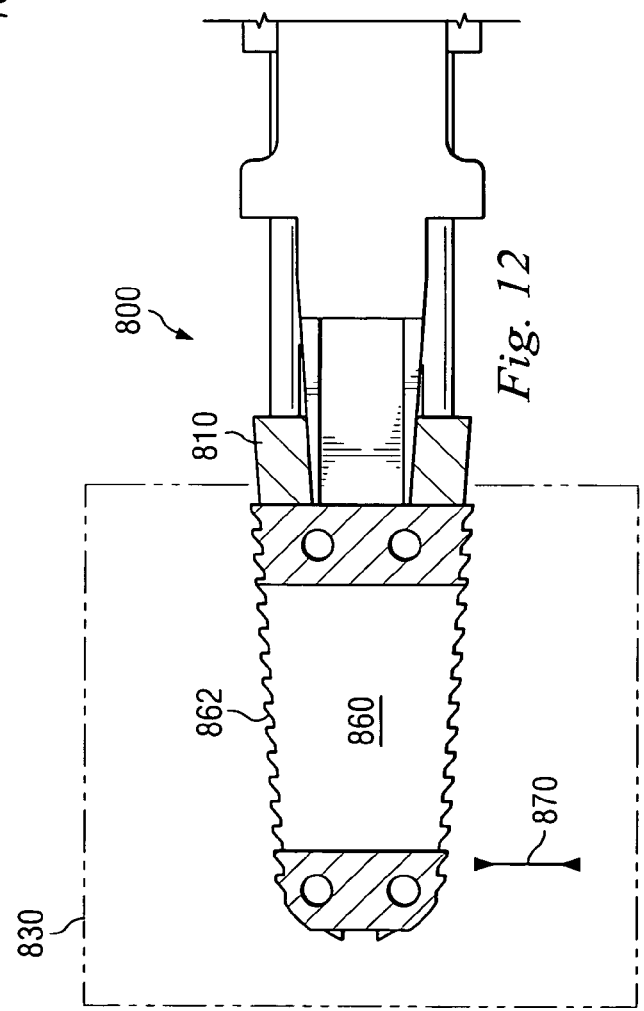
FIG. 12 is a cross-sectional side view of the embodiment shown in FIG. 11.

Referring now to FIG. 12, in another embodiment, there is illustrated a side cross-sectional view of distal end of tool 800 from FIG. 11. Distal end of tool 800 includes implant 860 and distractor tangs 810. Implant 860 includes rough surfaces 862. Implant 860 is shown held by distal end of tool 800. Distractor tangs 810 have closed medially, as shown by arrows 870, to expose rough surfaces 862 to tissue 830.

In another embodiment, insert 860 has a thickness greater than the opening created by distractors 810, so that rough surfaces 862 engage tissue 830.

Figure 13:
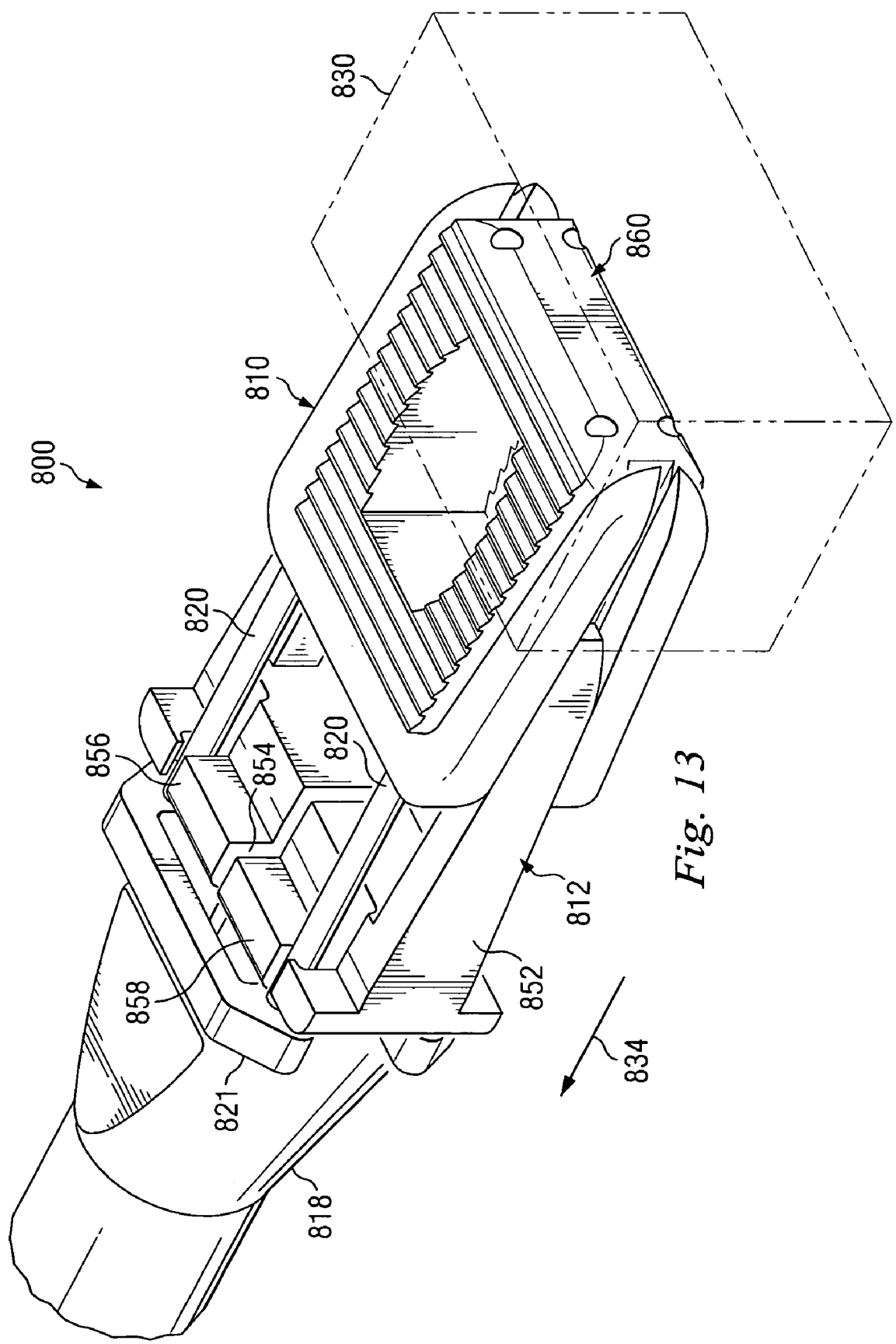
FIG. 13 is a perspective view of an embodiment of the distal end of a surgical instrument with an insert.

Referring now to FIG. 13, in another embodiment, there is illustrated distal end of tool 800 of FIG. 11. Distal end of tool 800 includes distractor tangs 810, inserter tangs 812, and distal end of compression tube 818. Distractor tangs 810 are attached to arms 820. Arms 820 are attached to arm connector 821.

In operation, implant 860 is shown sliding distally relative to left inserter tang 850 and right inserter tang 852, since tube 818 allowed left inserter bracket 856 and right inserter bracket 858 to open laterally, and open space 854. Proximal movement of tool 800 and inserter tangs 812 allows tissue 830 to force distractor tangs 810 to close medially. As inserter tangs 812 continue to move proximally, distractor tangs 810 continue to close medially, and expose insert 860 to tissue 830. Continued proximal movement of distal end of tool 800 causes left inserter bracket 856 and right inserter bracket 858 to engage arm connector 821, and pull distractor tangs 810 proximally, as shown by arrow 834, by arms 820 and arm connector 821.

Figure 14:
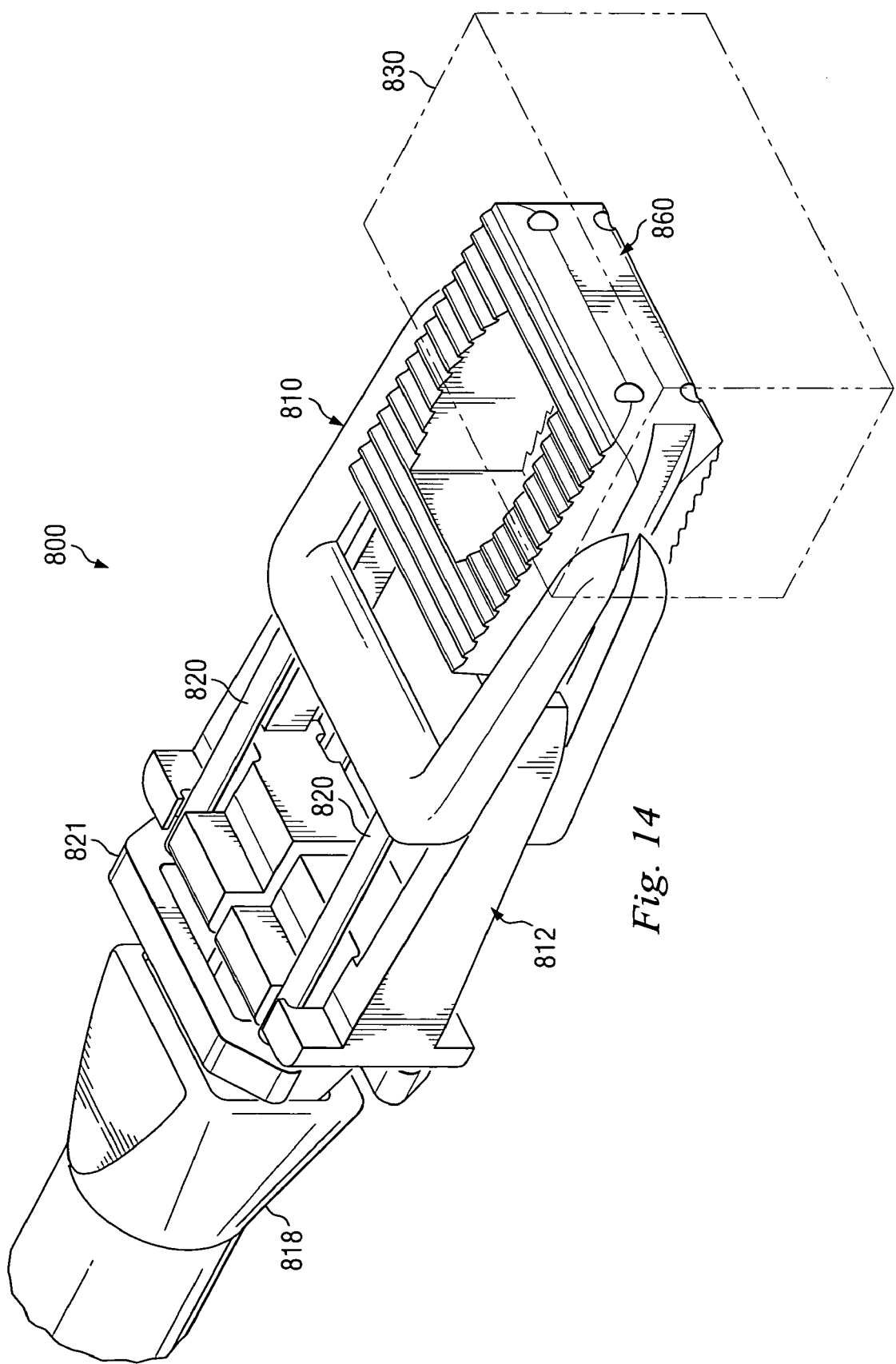
FIG. 14 is a perspective view of an embodiment of the distal end of a surgical instrument with an insert.

Referring now to FIG. 14, in another embodiment, there is illustrated distal end of tool 800 of FIG. 11. Distal end of tool 800 includes distractor tangs 810, inserter tangs 812, and distal end of compression tube 818. Distractor tangs 810 are attached to arms 820. Arms 820 are attached to arm connector 821.

In operation, continued proximal movement of distal end of tool 800 causes left inserter bracket 856 and right inserter bracket 858 to engage arm connector 821, and pull distractor tangs 810 proximally, as shown by arrow 834. This continued proximal movement pulls implant 860 away from distractor tangs 810, while leaving implant 860 engaged with tissue 830.

Figure 15:
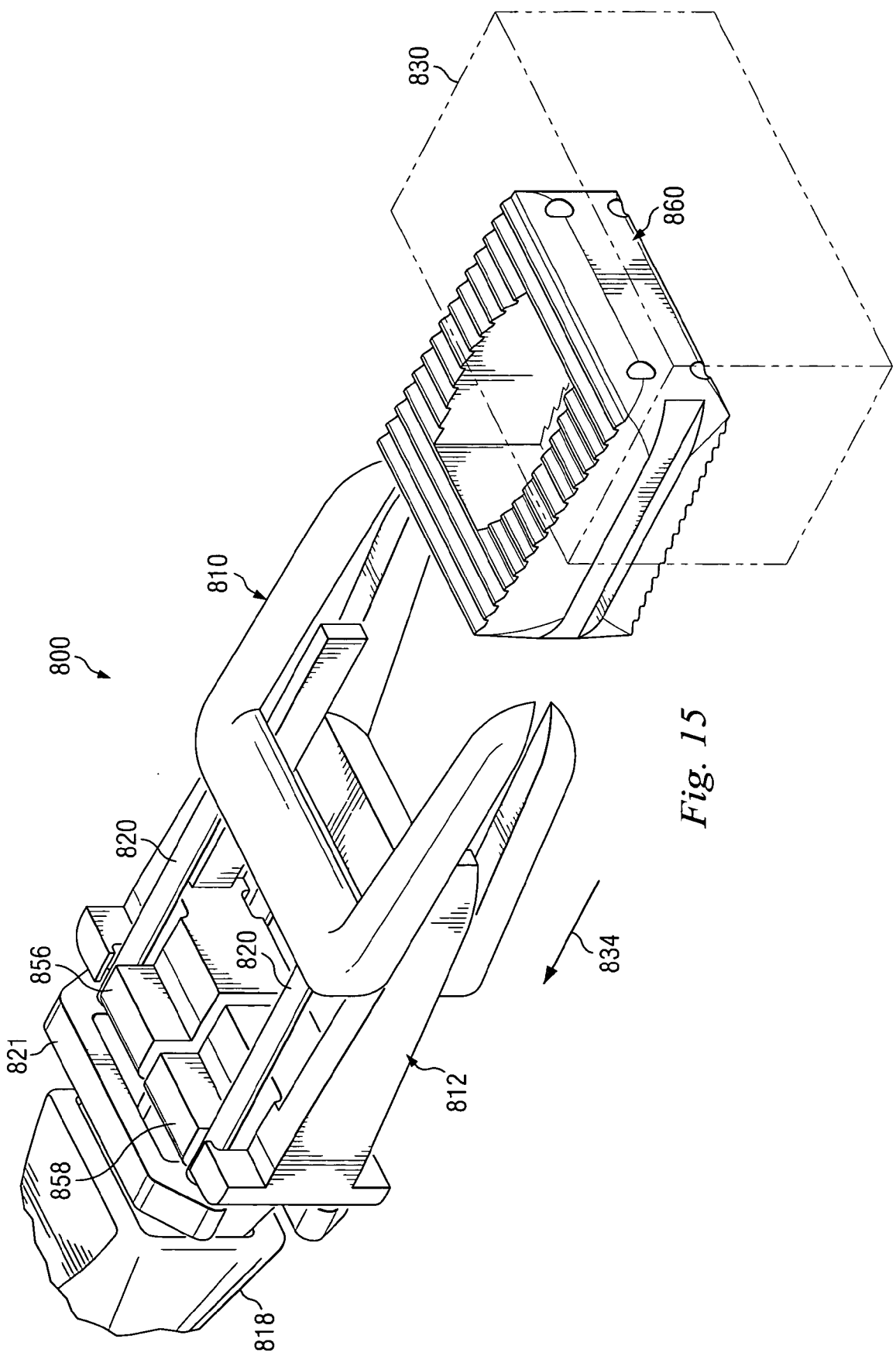
FIG. 15 is a perspective view of an embodiment of the distal end of a surgical instrument and an insert.

Referring now to FIG. 15, in another embodiment, there is illustrated distal end of tool 800 of FIG. 11. Distal end of tool 800 includes distractor tangs 810, inserter tangs 812, and distal end of compression tube 818. Distractor tangs 810 are attached to arms 820. Arms 820 are attached to arm connector 821.

In operation, continued proximal movement of distal end of tool 800 causes left inserter bracket 856 and right inserter bracket 858 to engage arm connector 821, and pull distractor tangs 810 proximally, as shown by arrow 834, by arms 820 and arm connector 821. This continued proximal movement completely disengages implant 860 from distractor tangs 810, while leaving implant 860 engaged with tissue 830.

In one embodiment, tissue 430, 630, and/or 830 may be the space between the end plates of adjacent vertebrae, for example L3 112 and L4 114. In another embodiment, tissue 430, 630, and/or 830 may be a partially removed or damaged intervertebral disc, for example disc 114. In another embodiment, tissue 430, 630, and/or 830 may be adjacent vertebrae, for example L3 112 and L4 114.

In one embodiment, there is disclosed a surgical instrument for inserting an implant, the surgical instrument including a tool having a shaft, an inserter assembly coupled to the shaft and configured for releasably holding the implant, and a distractor assembly coupled to the shaft and configured for providing an opening in a patient's tissue. In another embodiment, the shaft also includes a proximal end and a distal end, the inserter assembly and the distractor assembly disposed adjacent the distal end. In another embodiment, the shaft also includes a handle adjacent the proximal end. In another embodiment, the surgical instrument also includes a locking assembly configured to selectably lock and unlock the inserter assembly. In another embodiment, the shaft includes a proximal end and a distal end, the inserter assembly disposed adjacent the distal end, and the locking assembly disposed adjacent the proximal end. In another embodiment, the inserter assembly is movable between a locked position wherein said implant is locked within the inserter assembly, and an open position wherein said implant may be removed from said inserter assembly. In another embodiment, the distractor assembly is movable between a first opened position, and a second closed position. In another embodiment, the surgical instrument also includes the insert, the insert including a thickness less than the first opened position, and greater than the second closed position. In another embodiment, the distractor assembly is slidably engaged on the inserter assembly. In another embodiment, the distractor assembly is movable between a first opened position, and a second closed position; and wherein said inserter assembly is movable between a locked position wherein said implant is locked within the inserter assembly, and an open position wherein said implant may be removed from said inserter assembly.

In one embodiment, there is disclosed a method of inserting an implant into a patient's tissue, the method including holding the implant within an inserter assembly of a surgical instrument, distracting the tissue with a distractor assembly of the surgical instrument, releasing the implant from the inserter assembly, and releasing the distractor assembly to allow the tissue to engage the implant. In another embodiment, the method also includes removing the inserter assembly and the distractor assembly from the tissue.

In one embodiment, there is disclosed a surgical instrument for inserting an implant, the surgical instrument including an inserter means adapted to selectively hold and release the implant, and a distractor means adapted to provide an opening in a patient's tissue for passage of the inserter means. In another embodiment, the surgical instrument also includes a shaft, the shaft comprising a proximal end and a distal end, the inserter means and the distractor means disposed adjacent the distal end. In another embodiment, the shaft further comprises a handle adjacent the proximal end. In another embodiment, the surgical instrument also includes a locking means adapted to lock and unlock the inserter means. In another embodiment, the locking means is disposed adjacent the proximal end of the shaft. In another embodiment, the inserter means is movable between a locked position wherein said implant is locked within the inserter means, and an open position wherein said implant may be removed from said inserter means. In another embodiment, the distractor means is movable between a first opened position, and a second closed position. In another embodiment, the surgical instrument also includes the insert, the insert comprising a thickness less than the first opened position, and greater than the second closed position. In another embodiment, the distractor means is movable between a first opened position, and a second closed position; and wherein said inserter means is movable between a locked position wherein said implant is locked within the inserter means, and an open position wherein said implant may be removed from said inserter means.

The above-described embodiments of the present disclosure include a number of reference numerals provided to aid in the understanding of the disclosed devices. Although the same and similar reference numerals have been used in multiple figures and for multiple embodiments for the sake of convenience, it should not be assumed that the same reference numeral refers to the same element or that similarly numbered elements are the same element in each of the figures and embodiments.

The above description of the embodiments according to the disclosure are merely exemplary in nature and, thus, variations that do not depart from the gist of the invention are intended to be within the scope of the invention. Such variations are not to be regarded as a departure from the spirit and scope of the invention.

What is claimed is:

1. A surgical instrument for inserting an implant between adjacent vertebrae of a spine, the instrument comprising:
   a handle coupled to a proximal end of a shaft, the shaft having a longitudinal axis and an opposite distal end,
   a first inserter arm coupled to the distal end of the shaft, the first inserter arm having a first driving shoulder extending outwardly generally perpendicular to the longitudinal axis, and a first inserter tang projecting distally from said first driving shoulder;
   a second inserter arm coupled to the distal end of the shaft and defining an implant receiving recess between the first inserter arm and the second inserter arm; and
   a distractor assembly mounted on said first inserter arm, said distractor assembly comprising a retention base having at least one distally projecting distractor tang, at least one distractor arm coupled to said retention base, and a distractor arm connector coupled to said distractor arm, said distractor arm slidably joined to the first shoulder,
   wherein movement of the distractor assembly distally along the longitudinal axis is limited by the abutting engagement of the distractor arm connector with the first driving shoulder and movement proximally of the distractor assembly is limited by the abutting engagement of the retention base with the first driving shoulder.

2. The instrument of claim 1, wherein the first distractor assembly is positioned to face a superior vertebra and further comprising a second driving shoulder extending outwardly generally perpendicular to the longitudinal axis from the second inserter arm, and a second inserter tang projecting distally from said second driving shoulder; and
   a second distractor assembly mounted on said shaft to face an inferior vertebra, the second distractor assembly comprising a second retention base having at least one distally projecting inferior distractor tang, at least one second distractor arm coupled to said second retention base, and a second distractor arm connector coupled to said second distractor arm and slidably joined to the second shoulder,
   wherein movement of the second distractor assembly distally along the longitudinal axis is limited by the abutting engagement of the second distractor arm connector with the second driving shoulder and movement proximally of the second distractor assembly is limited by the abutting engagement of the second retention base with the second driving shoulder.

3. The instrument of claim 2, wherein the first and second driving shoulders each have a longitudinal slot penetrating therethrough, the slots adapted to slidably retain the distractor arm of the first distractor assembly and the second distractor arm of the second distractor assembly, respectively.

4. The instrument of claim 3, wherein the upper and lower second driving shoulders each have a second longitudinal slot penetrating therethrough, the slots adapted to slidably retain a second pair of upper and lower distractor arms which are coupled on first ends to respective upper and lower retention bases and on second ends to upper and lower distractor arm connectors.

5. The instrument of claim 1, wherein said shaft includes a longitudinal slot formed adjacent said distal end such that said first inserter arm and said second inserter arm may be moved from an engaged position to hold the implant to a released position spaced from the implant, and further comprising a compression member mounted on said shaft to move the first and second inserter arms into the engaged position.

6. A surgical instrument for inserting an implant in a space between adjacent vertebrae of a spine, the instrument comprising:
- a shaft having a longitudinal axis extending between a distal end and a proximal end, the distal end comprising an inserter portion having first and second inserter tangs movable between an engaged position for laterally grasping the implant and a released position for releasing the implant, the inserter tangs including first and second inserter brackets joined to the shaft, each first and second inserter bracket defining an outwardly projecting flange having a proximal abutment face and an opposing distal abutment face;
- a distractor assembly mounted on the distal end of said shaft and slidably coupled to the inserter portion to permit movement along the longitudinal axis of the shaft, the distractor assembly movable along the longitudinal axis between a distraction position having a first height for creating an opening between the adjacent vertebrae for the implant and a retraction position having a second height less than the first height, the distractor assembly movement towards the distraction position limited by abutting engagement between the distractor assembly and the distal abutment faces of the first and second inserter brackets, and the distractor assembly movement towards the retraction position limited by abutting engagement between the distractor assembly and the proximal abutment face of the first and second inserter brackets; wherein the inserter portion is configured for holding the implant in a fixed longitudinal position relative to the longitudinal position of the distractor assembly during insertion of the implant in the space between adjacent vertebrae; and
- a compression sleeve mounted about said shaft and adapted to move the first and second inserter tangs between the engaged position and the released position.

7. The instrument of claim 6, further comprising a locking assembly configured to selectively lock a longitudinal position of the compression sleeve to maintain the first and second inserter tangs in the engaged position.

8. The instrument of claim 7, wherein the locking assembly includes a cam lever.

9. A surgical instrument for inserting an implant in a space between adjacent vertebrae of a spine, the instrument comprising:
- a shaft having a longitudinal axis extending between a distal end and a proximal end, the distal end comprising an inserter portion having first and second inserter tangs movable between an engaged position for laterally grasping the implant and a released position for releasing the implant, the inserter tangs including first and second inserter brackets joined to the shaft, each first and second inserter bracket defining an outwardly projecting flange having a proximal abutment face and an opposing distal abutment face; and
- a distractor assembly mounted on the distal end of said shaft and slidably coupled to the inserter portion to permit movement along the longitudinal axis of the shaft, the distractor assembly movable along the longitudinal axis between a distraction position having a first height for creating an opening between the adjacent vertebrae for the implant and a retraction position having a second height less than the first height, the distractor assembly movement towards the distraction position limited by abutting engagement between the distractor assembly and the distal abutment faces of the first and second inserter brackets, and the distractor assembly movement towards the retraction position limited by abutting engagement between the distractor assembly and the proximal abutment face of the first and second inserter brackets; wherein the inserter portion is configured for holding the implant in a fixed longitudinal position relative to the longitudinal position of the distractor assembly during insertion of the implant in the space between adjacent vertebrae,
wherein the first inserter tang has a first length, and a total longitudinal travel distance of the distractor assembly between the distraction position and the retraction position is less than said first length.

* * * * *

UNITED STATES PATENT AND TRADEMARK OFFICE
CERTIFICATE OF CORRECTION

PATENT NO.        : 7,625,380 B2                                    Page 1 of 1
APPLICATION NO. : 10/896290
DATED             : December 1, 2009
INVENTOR(S)       : Drewry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1039 days.

Signed and Sealed this

Twenty-sixth Day of October, 2010

David J. Kappos
*Director of the United States Patent and Trademark Office*